United States Patent
Gonopolskiy et al.

(10) Patent No.: US 8,670,812 B2
(45) Date of Patent: Mar. 11, 2014

(54) PHYSIOLOGICAL SENSOR HAVING A WAIST

(75) Inventors: Oleg Gonopolskiy, West Bloomfield, MI (US); Arik Anderson, Birmingham, MI (US); Melissa Muto, Royal Oak, MI (US); Richard Morbito, Grosse Ile, MI (US); Matthew Stimpson, Macomb, MI (US)

(73) Assignee: Covidien LP, Mansfield, MA (US)

( * ) Notice: Subject to any disclaimer, the term of this patent is extended or adjusted under 35 U.S.C. 154(b) by 666 days.

(21) Appl. No.: 12/842,801

(22) Filed: Jul. 23, 2010

(65) Prior Publication Data
US 2011/0021893 A1 Jan. 27, 2011

Related U.S. Application Data

(60) Provisional application No. 61/228,086, filed on Jul. 23, 2009.

(51) Int. Cl.
*A61B 5/00* (2006.01)
(52) U.S. Cl.
USPC .................................................. 600/323
(58) Field of Classification Search
USPC .................................................. 600/323
See application file for complete search history.

(56) References Cited

U.S. PATENT DOCUMENTS

| | | | |
|---|---|---|---|
| 6,519,484 B1 * | 2/2003 | Lovejoy et al. | 600/323 |
| 6,745,061 B1 * | 6/2004 | Hicks et al. | 600/344 |
| 2005/0197550 A1 * | 9/2005 | Al-Ali et al. | 600/323 |
| 2005/0251004 A1 * | 11/2005 | Istvan et al. | 600/395 |
| 2006/0084852 A1 * | 4/2006 | Mason et al. | 600/344 |
| 2006/0089585 A1 * | 4/2006 | Takemura et al. | 602/58 |
| 2007/0197886 A1 * | 8/2007 | Naganuma et al. | 600/322 |
| 2008/0242958 A1 * | 10/2008 | Al-Ali et al. | 600/323 |
| 2009/0143657 A1 * | 6/2009 | Diab et al. | 600/344 |
| 2009/0182209 A1 * | 7/2009 | Benni | 600/323 |
| 2010/0049018 A1 * | 2/2010 | Duffy et al. | 600/323 |
| 2012/0046530 A1 * | 2/2012 | Al-Ali et al. | 600/310 |

* cited by examiner

*Primary Examiner* — Rodney Fuller

(57) ABSTRACT

An exemplary sensor includes a sensor pad having a first portion and a second portion separated by a waist portion. The waist portion is narrower than the first portion and the second portion. A light source that is disposed on the first portion is configured to generate near-infrared light and transmit the near-infrared light through part of a patient's body. A light detector that is disposed on the second portion is configured to detect near-infrared light that has traveled through the part of the patient's body. The near-infrared light detected indicates an amount of oxygen in the part of the patient's body through which the near-infrared light traveled.

22 Claims, 2 Drawing Sheets

PHYSIOLOGICAL SENSOR HAVING A WAIST

CROSS-REFERENCE TO RELATED APPLICATIONS

This application claims priority to U.S. Ser. No. 61/228,086 filed Jul. 23, 2009, which is incorporated herein by reference in its entirety.

BACKGROUND

Near-infrared sensors are used in the medical industry to measure the amount of oxygen saturation in a patient's blood or tissue. These sensors work by detecting light after it has traveled through a portion of the patient's body. However, ambient or other light may interfere with the sensor, providing medical personnel with false readings that may lead to missed diagnoses and incorrect treatments. Existing solutions to blocking ambient light results in sensors that are bulky and expensive to manufacture. Moreover, these bulky sensors are not very flexible and cannot always conform to the contours of a patient's body. Accordingly, a physiological sensor is needed that protects against interference from ambient and other forms of light but is flexible enough to conform to the contours of the patient's body.

DETAILED DESCRIPTION

An exemplary physiological sensor that blocks interfering light and provides sufficient flexibility includes a sensor pad having a first portion and a second portion separated by a waist portion. The waist portion is narrower than the first portion and the second portion. A light source disposed on the first portion is configured to generate near-infrared light and transmit the near-infrared light through part of a patient's body. A light detector disposed on the second portion is configured to detect near-infrared light that has traveled through the part of the patient's body. The near-infrared light detected indicates an amount of oxygen in the part of the patient's body through which the near-infrared light traveled.

Figure 1:
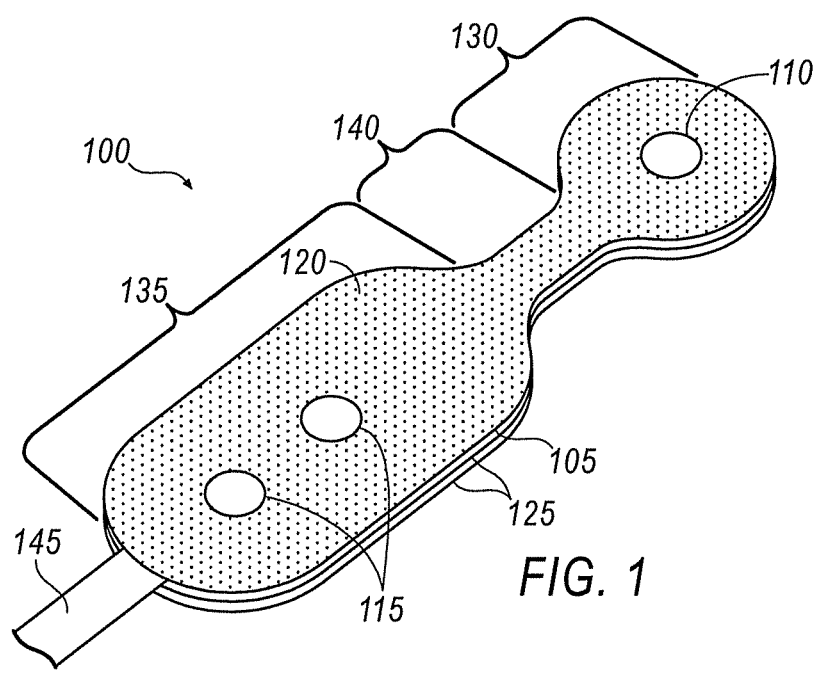
FIG. 1 illustrates an exemplary sensor having a sensor pad with a waist portion.

FIG. 1 illustrates an exemplary sensor 100 that conforms to the contours of a patient's body and is able to prevent interference from ambient light. The sensor 100 may take many different forms and include multiple and/or alternate components and facilities. While an exemplary sensor 100 is shown in FIG. 1, the exemplary components illustrated in the figures are not intended to be limiting. Indeed, additional or alternative components and/or implementations may be used.

Figure 2:
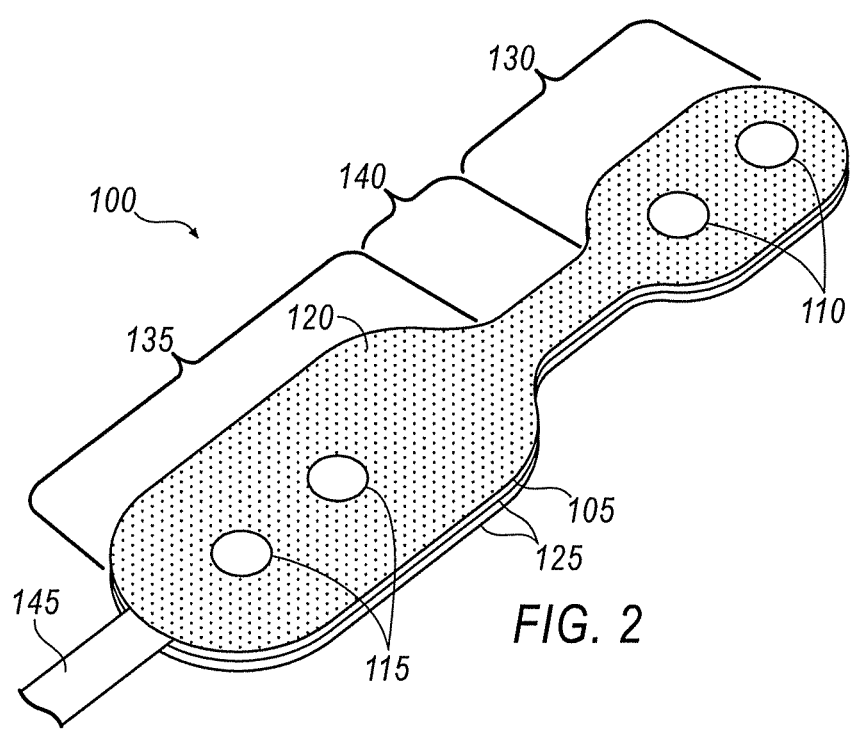
FIG. 2 illustrates an exemplary sensor having another sensor pad with a waist portion.

As illustrated in FIG. 1, the sensor 100 includes a sensor pad 105 housing a light source 110 and a light detector 115. Of course, the sensor pad 105 may house any number of light sources 110 and light detectors 115. Indeed, one light source 110 and two light detectors 115 are illustrated in FIG. 1. FIG. 2 illustrates a sensor 100 with two light sources 110 and two light detectors 115. As illustrated in FIGS. 1 and 2, the sensor 100 may further include an adhesive 120 disposed on the sensor pad 105 and a connector 145.

The sensor pad 105 may be formed from any material configured to house the light source 110 and light detector 115. For instance, the sensor pad 105 may be formed from two or more layers 125 of a flexible material that sandwich one or more circuit boards (not shown) with the light source 110, the light detector 115, or both. At least one of the layers 125 may include a light blocking material. That is, one of the layers 125 may be opaque to ambient and other types of light that may interfere with the light detector 115. When placed on a patient, one layer 125 is disposed on the patient's skin while the other layer 125 is spaced from the patient's skin. In one exemplary approach, the layer 125 spaced from the patient's skin includes the light blocking material. Of course, both layers 125 may include the light blocking material and the layer 125 disposed on the patient's skin may define openings in line with the light source 110 and light detector 115. Further, one or both of the layers 125 may include a flexible material so that the sensor 100 may bend to fit the contours of the patient's body.

The sensor pad 105 may define a first portion 130 that may house the light source 110 and/or the light detector 115, a second portion 135 that may house the light source 110 and/or the light detector 115, and a waist portion 140 that separates the first portion 130 and the second portion 135. The first portion 130, the second portion 135, and the waist portion 140 may be integrally formed with one another from the layers 125 of the sensor pad 105. Additionally, the first portion 130, the second portion 135, the waist portion 140, or any combination thereof, may include the light blocking material and/or the flexible material. In one exemplary approach, only the second portion 135 includes the light blocking material and only the waist portion 140 includes the flexible material. However, in the interest of reducing manufacturing complexity, each of the first portion 130, the second portion 135, and the waist portion 140 may include both the light blocking material and the flexible material.

The second portion 135 may have a larger surface area than the first portion 130 and the waist portion 140. The larger surface area helps the sensor pad 105 block interfering light, such as ambient light. With the larger surface area, it is less likely that the light detector 115 will receive interfering light and provide false oximetry readings. Since the light source 110 does not need protection against interfering light, manufacturing the sensor 100 so that the first portion 130 has a smaller surface area than the second portion 135 results in reduced material costs. Alternatively, however, the second portion 135 and the first portion 130 may have the same surface area.

The waist portion 140 may be narrower than the first portion 130 and the second portion 135 to provide the sensor 100 with additional flexibility to fit the contours of the patient. In one exemplary implementation, the first portion 130 and the second portion 135 may gradually taper to the width of the waist portion 140, thus providing a smooth transition between the first portion 130, the waist portion 140, and the second portion 135. Alternatively, one or both of the first portion 130 and the second portion 135 may transition to the waist portion 140 more abruptly.

The light source 110 may include any device that is able to generate near-infrared light. For instance, the light source 110 may include a light emitting diode (LED) or a laser diode. Of course, the light source 110 may include additional or alternative devices. Further, the sensor 100 may include any number of light sources 110. For example, as illustrated in FIG. 2, the sensor 100 includes two light sources 110 within the first portion 130.

The light detector 115 may include any device configured to detect near-infrared light. The light detector 115, therefore, may include a photodiode. Any number of light detectors 115 may be disposed on the sensor pad 105. As illustrated in FIGS. 1 and 2, the sensor pad 105 houses two light detectors 115.

The adhesive 120 is disposed on the layer 125 of the sensor pad 105 that will be disposed on the patient while the sensor 100 is in use. The adhesive 120 may include any adhesive 120 that is able to hold the sensor pad 105 in place relative to the patient's body. For example, the adhesive 120 may include a pressure sensitive adhesive 120.

The connector 145 may extend from the sensor pad 105 and be used to control the light source 110 and light detector 115. Moreover, the connector 145 may transmit signals representing the light received by the light detector 115 to a controller (not shown) for further processing.

Figure 3:
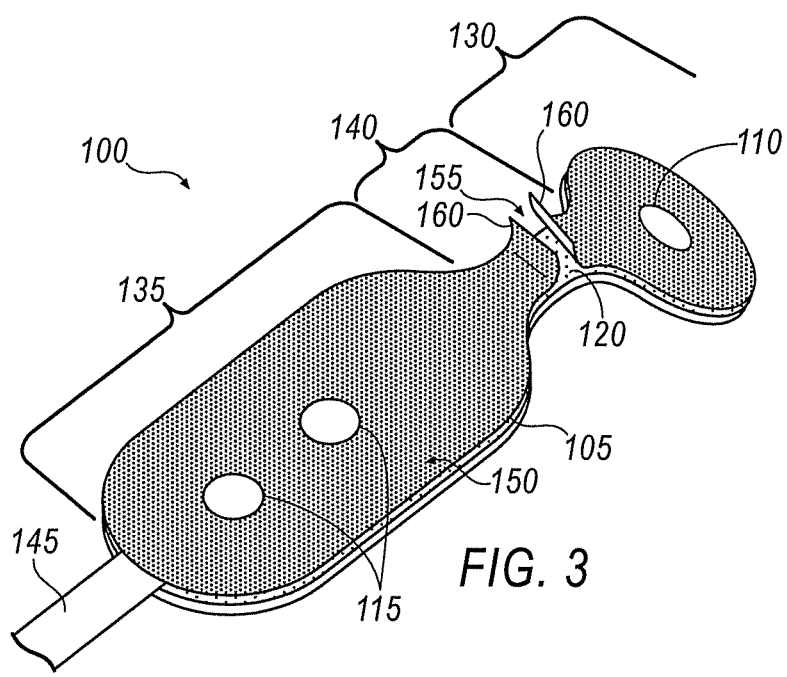
FIG. 3 illustrates an exemplary sensor having a liner disposed on the sensor pad.

FIG. 3 illustrates an exemplary sensor 100 having a liner 150 disposed on the adhesive 120. The liner 150 may, for example, prevent the adhesive 120 from adhering the sensor pad 105 to unintended objects until the sensor 100 is ready to be placed on a patient. The liner 150 may be formed from any material that adheres to the adhesive 120 but will not significantly remove the adhesive 120 when the liner 150 is removed. The liner 150 may be formed from one or more pieces. For instance, in the exemplary approach of FIG. 3, the liner 150 is formed from two pieces.

The liner 150 defines a slit 155 over the waist portion 140. The slit 155 and flexibility of the waist portion 140 may allow a user of the sensor 100 to easily remove the liner 150. For instance, the user may bend the waist portion 140 as illustrated in FIG. 3 to expose two tabs 160. The user may further pull each tab 160 to remove each piece of the liner 150 from the sensor 100. Removing the liner 150 exposes the adhesive 120. With the liner 150 removed, the user may adhere the sensor 100 to the patient.

Figure 4:
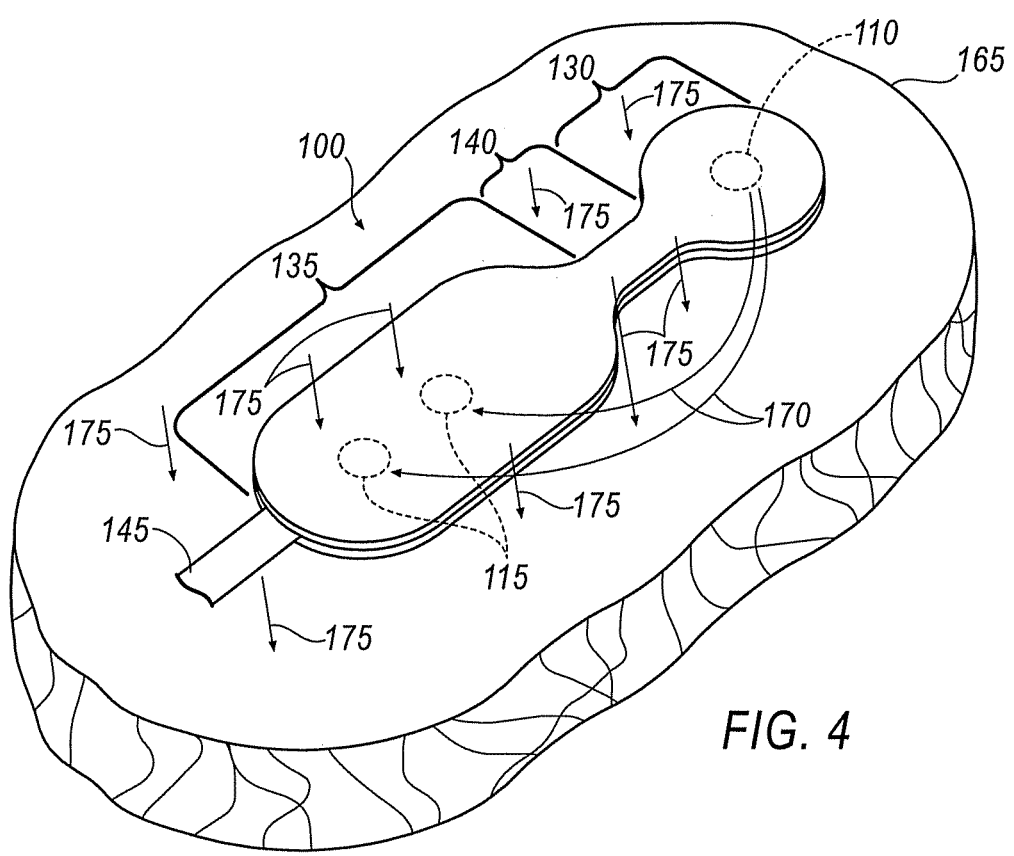
FIG. 4 illustrates the exemplary sensor of FIG. 1 disposed on a patient.

FIG. 4 illustrates the sensor 100 disposed on a patient. As illustrated, the near-infrared light 170 from the light source 110 is transmitted through blood or tissue and is received by the light detector 115. The light detector 115 generates a signal that indicates the oxygen saturation of the blood or tissue through which the light 170 traveled. The second portion 135 of the sensor pad 105 has a larger surface area than the first portion 130. While some interfering light 175 such as ambient light may travel through the tissue, the large surface area of the second portion 135 reduces the amount of interfering light 175 that is received by the sensor 100. FIG. 4 further illustrates the waist portion 140 that is narrower than the first portion 130 and the second portion 135. This gives the sensor 100 additional flexibility to fit the contours of the patient's body.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent upon reading the above description. The scope of the invention should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the invention is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A sensor comprising:
   an integrated sensor pad having a first portion and a second portion separated by a waist portion, wherein the waist portion is narrower than the first portion and the second portion, and wherein said sensor pad is configured to be adhered to a patient's body by an adhesive disposed directly on an underside of said sensor pad;
   a light source at least partially housed within said sensor pad and configured to generate near-infrared light and transmit the near-infrared light through part of a patient's body; and
   a light detector at least partially housed within said sensor pad and configured to detect near-infrared light that has traveled through the part of the patient's body, wherein the near-infrared light detected indicates an amount of oxygen in the part of the patient's body through which the near-infrared light traveled.

2. A sensor as set forth in claim 1, wherein the second portion is configured to substantially prevent the light detector from receiving interfering light.

3. A sensor as set forth in claim 1, wherein at least one of the first portion, the waist portion, and the second portion includes a light blocking material.

4. A sensor as set forth in claim 1, further comprising a liner disposed on the adhesive.

5. A sensor as set forth in claim 4, wherein the liner defines a slit.

6. A sensor as set forth in claim 5, wherein the slit is located over the waist portion to facilitate removal of the liner.

7. A sensor as set forth in claim 1, wherein at least one of the first portion, the second portion, and the waist portion includes a flexible material.

8. A sensor as set forth in claim 1, wherein the light detector is disposed on the second portion and wherein the second portion has a larger surface area than the first portion.

9. A sensor as set forth in claim 1, wherein the sensor pad is formed from multiple layers having generally the same size and shape and forming the first portion, the second portion, and the waist portion.

10. A sensor pad comprising:
    a first portion configured to house a light source that generates near-infrared light and transmits the near-infrared light through a part of a patient's body;
    a second portion configured to house a light detector that detects near-infrared light after the near-infrared light has traveled through a part of the patient's body, wherein the light received indicates oxygen saturation of the part of the patient's body through which the light traveled; and a waist portion disposed between the first portion and the second portion, wherein the surface area of the second portion is larger than the surface area of the first portion and the waist portion is narrower than the first portion and the second portion.

11. A sensor pad as set forth in claim 10, wherein the second portion includes a light blocking material that substantially prevents the light detector from receiving interfering light.

12. A sensor pad as set forth in claim 10, wherein at least one of the first portion and the waist portion include a light blocking material.

13. A sensor pad as set forth in claim 10, wherein the waist portion includes a flexible material.

14. A sensor pad as set forth in claim 10, wherein at least one of the first portion and the second portion includes a flexible material.

15. A sensor pad as set forth in claim 10, further comprising an adhesive disposed on an underside of the first portion and the second portion.

16. A sensor pad as set forth in claim 15, further comprising a liner disposed on the adhesive.

17. A sensor pad as set forth in claim 16, wherein the liner defines a slit located over the waist portion to facilitate removal of the liner.

18. A sensor pad as set forth in claim 10, wherein said sensor pad comprises a plurality of layers and each of the layers is substantially the same size and shape.

19. A sensor comprising:

an integrated sensor pad assembly having a plurality of layers having generally the same size and shape and forming a first portion and a second portion separated by a waist portion, wherein the waist portion is narrower than the first portion and the second portion, the second portion including a light blocking material and the waist portion including a flexible material;

a light source disposed on the first portion and configured to generate near-infrared light and transmit the near-infrared light through a part of a patient's body;

a light detector disposed on the second portion and configured to detect near-infrared light that has traveled through part of the patient's body to identify an amount of oxygen in the part of the patient's body through which the near-infrared light traveled, and wherein the second portion substantially prevents the light detector from receiving interfering light;

an adhesive disposed directly on the sensor pad; and a liner disposed on the adhesive and defining a slit located near or over the waist portion.

20. A sensor as set forth in claim 19, wherein at least one of the first portion, the second portion, and the waist portion includes a flexible material.

21. A sensor as set forth in claim 19, wherein the second portion of the sensor pad assembly has a larger surface area than the first portion.

22. A sensor as set forth in claim 19, wherein said first portion has a surface area that is smaller than the surface area of the second portion.

* * * * *